United States Patent
Nagy

(10) Patent No.: US 6,414,162 B1
(45) Date of Patent: Jul. 2, 2002

(54) BIMETALLIC CATALYSTS FOR OLEFIN POLYMERIZATION

(75) Inventor: Sandor Nagy, Mason, OH (US)

(73) Assignee: Equistar Chemicals, LP, Houston, TX (US)

(*) Notice: Subject to any disclaimer, the term of this patent is extended or adjusted under 35 U.S.C. 154(b) by 0 days.

(21) Appl. No.: 09/826,545

(22) Filed: Apr. 5, 2001

(51) Int. Cl.[7] .............................. B01J 31/18; C07F 7/02
(52) U.S. Cl. ...................... 548/406; 526/160; 526/161; 502/155
(58) Field of Search .................. 548/402; 526/160, 526/161; 502/155

(56) References Cited

U.S. PATENT DOCUMENTS

| | | | |
|---|---|---|---|
| 5,153,157 A | 10/1992 | Hlatky et al. | 502/117 |
| 5,198,401 A | 3/1993 | Turner et al. | 502/155 |
| 5,241,025 A | 8/1993 | Hlatky et al. | 526/129 |
| 5,539,124 A | 7/1996 | Etherton et al. | 548/402 |
| 5,554,775 A | 9/1996 | Krishnamurti et al. | 556/7 |
| 5,902,866 A | 5/1999 | Nagy et al. | 526/133 |
| 6,232,260 B1 | 5/2001 | Nagy et al. | 502/155 |

FOREIGN PATENT DOCUMENTS

WO    WO 99/24446    5/1999

OTHER PUBLICATIONS

Ng. Buu–Hoi et al., *J. Chem. Soc.* (1952) 2225.
T. Abraham, *Monatsh. Chem.* 120 (1989) 117.
T. Abraham et al., *Tetrahedron* 38 (1982) 1019.
F. Carey et al., *Advanced Organic Chemistry, Part B.* (1977), pp. 418–423.

*Primary Examiner*—Ceila Chang
*Assistant Examiner*—Andrea D. Small
(74) *Attorney, Agent, or Firm*—Jonathan L. Schuchardt

(57) ABSTRACT

Catalyst systems useful for olefin polymerization are disclosed. The catalyst systems include an activator and an organometallic complex. The complex, which incorporates at least one Group 3–10 transition or lanthanide metal, is uniquely prepared from an indenoindolyl dianion or its synthetic equivalent. A diverse array of monomeric, dimeric, polymeric, or zwitterionic complexes are available from the dianion or its equivalent.

20 Claims, No Drawings

BIMETALLIC CATALYSTS FOR OLEFIN POLYMERIZATION

FIELD OF THE INVENTION

The invention relates to catalysts useful for olefin polymerization. In particular, the catalysts incorporate dianionic indenoindolyl ligands and at least one Group 3–10 transition or lanthanide metal atom.

BACKGROUND OF THE INVENTION

While Ziegler-Nafta catalysts are a mainstay for polyolefin manufacture, metallocenes and similar catalysts are the industry's future. Metallocenes typically include a transition metal and at least one cyclopentadienyl or substituted cyclopentadienyl ligand. More recently, a number of non-metallocene, single-site catalysts have also been reported. Some of these catalysts replace the cyclopentadienyl groups of metallocenes with one or more heteroatomic ring ligands such as boraaryl (U.S. Pat. No. 5,554,775), indolyl or pyrrolyl (U.S. Pat. No. 5,539,124), or azaborolinyl groups (U.S. Pat. No. 5,902,866).

Organometallic complexes that incorporate one transition metal and at least one indenoindolyl ligand have also been described (see PCT Int. App. WO 99/24446 and U.S. Pat. No. 232,260). These complexes are normally made by reacting a transition metal source (e.g. zirconium tetrachloride) with one or two equivalents of an indenoindolyl monoanion. The monoanion is conveniently made by reacting a suitable precursor with about one equivalent of a potent base, such as n-butyllithium or methylmagnesium bromide.

Deprotonation removes an acidic proton from the methylene carbon of the cyclopentadiene fragment:

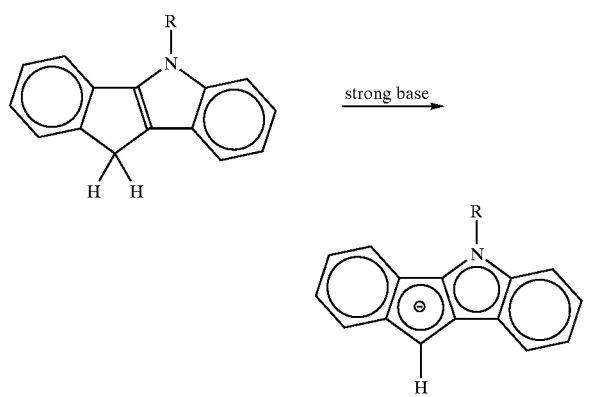

The indenoindolyl monoanion is a π-electron donor ligand that can displace labile anionic groups (e.g., a halide) from a transition metal compound to produce an indenoindolyl metal complex:

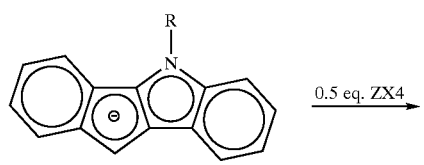

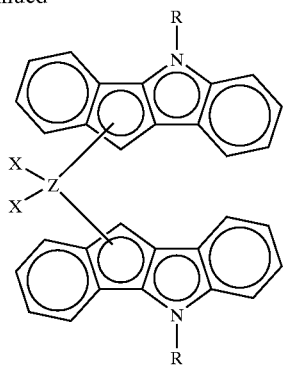

In the literature examples, R is usually an alkyl or aryl group. in the examples of PCT Int. Appl. WO 99/24446 in which an indenoindolyl transition metal complex is made, R is almost exclusively methyl or phenyl. In the examples of U.S. Pat. No. 6,232,260, R is methyl (see Examples A and B). The reported complexes are normally combined with an activator, such as methyl alumoxane, and are then used to polymerize olefins such as ethylene, or mixtures of ethylene and other α-olefins.

Missing from the literature is any suggestion to make complexes from indenoindolyl ligand precursors that have a hydrogen atom attached to the indole nitrogen. A unique and potentially valuable attribute of these ligand precursors is their ability to form dianions upon deprotonation with two equivalents of a strong base. Until now, such dianionic ligands have not been incorporated into transition metal complexes.

SUMMARY OF THE INVENTION

In one aspect, the invention is an organometallic complex which comprises at least one Group 3–10 transition or lanthanide metal and at least one dianionic indenoindolyl ligand that is pi- or sigma-bonded to the metal. The invention includes complexes produced from a dianionic indenoindolyl ligand that is generated from a synthetic equivalent. Catalyst systems of the invention comprise the complex and an activator, which is preferably an alkyl alumoxane. Also included is a method which comprises polymerizing an olefin in the presence of a catalyst system of the invention.

Indenoindolyl dianions and their synthetic equivalents are remarkably versatile. As described below, they can be used to produce a diverse assortment of monomeric, dimeric, and even polymeric or zwitterionic complexes that incorporate one or more transition metal atoms or a combination of transition metal and Group 13 atoms. When used with an activator, the complexes are valuable olefin polymerization catalysts.

DETAILED DESCRIPTION OF THE INVENTION

Organometallic complexes useful for catalyst systems of the invention comprise at least one Group 3–10 transition or lanthanide metal atom and at least one dianionic indenoindolyl ligand. Preferred complexes include a Group 4 to 6 transition metal; most preferably, the complex contains a Group 4 metal such as titanium or zirconium.

Dianionic indenoindolyl ligands are produced by reacting two equivalents of a potent base with an indenoindole compound. By "indenoindole compound," we mean an organic compound that has both indole and indene rings.

The five-membered rings from each are fused, i.e., they share two carbon atoms. Preferably, the rings are fused such that the indole nitrogen and the only sp³-hybridized carbon on the indenyl ring are "trans" to each other. Such is the case in an indeno[1,2-b] ring system such as:

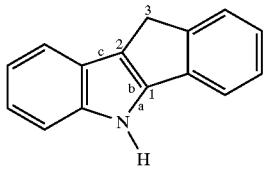

Suitable ring systems also include those in which the indole nitrogen and the sp³-hybridized carbon of the indene are beta to each other, i.e., they are on the same side of the molecule. This is an indeno[2,1-b]indole ring system:

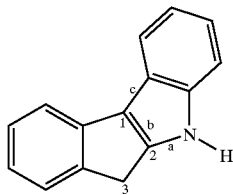

The ring atoms can be unsubstituted or substituted with one or more groups such as alkyl, aryl, aralkyl, halogen, silyl, nitro, dialkylamino, diarylamino, alkoxy, aryloxy, thioether, or the like. Additional fused rings can be present, as long as an indenoindole moiety is present.

When the indenoindole is used to make a dianionic ligand, it must have both an unsubstituted nitrogen (i.e., it has a hydrogen atom attached to nitrogen) and at least one hydrogen atom on the indenyl methylene carbon.

Numbering of indenoindoles follows IUPAC Rule A-22. The molecule is oriented as shown below, and numbering is done clockwise beginning with the ring at the uppermost right of the structure in a manner effective to give the lowest possible number to the heteroatom. Thus, 5,10-dihydroindeno[1,2-b]indole is numbered as follows:

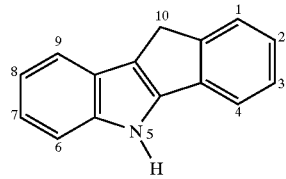

while 5,6-dihydroindeno[2,1-b]indole has the numbering:

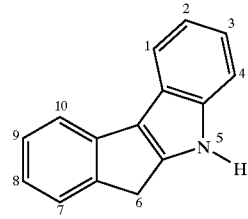

For correct nomenclature and numbering of these ring systems, see the Ring System Handbook (1998), a publication of Chemical Abstracts Service, Ring Systems File II: RF 33986-RF 66391 at RF 58952. (Note that indenoindoles are incorrectly numbered in U.S. Pat. No. 6,232,260; more correct numbering appears in PCT Int. Appl. WO 99/24446.

Suitable indenoindole compounds that are precursors to indenoindolyl dianions and their synthetic equivalents include, for example, 5,10-dihydroindeno[1,2-b]indole, 5,6-dihydroindeno[2,1-b]indole, 4,7-dimethyl-5,10-dihydroindeno[1,2-b]indole, 4-tert-butyl-8-methyl-5,10-dihydroindeno[1,2-b]indole, 4,8-dichloro-5,10-dihydroindeno-[1,2-b]indole, 2,7-dimethyl-5,6-dihydroindeno[2,1-b]indole, and the like.

Methods for making indenoindole compounds are well known. Suitable methods are disclosed. for example, in U.S. Pat. No. 6,232,260, the teachings of which are incorporated herein by reference, and references cited therein, including the method of Buu-Hoi and Xuong, J. Chem. Soc. (952) 2225. Suitable procedures also appear in Int. Appl. WO 99/24446.

Indenoindolyl dianions can be generated by deprotonating an indenoindole compound with two equivalents of a strong base. Suitable bases include alkali metals (e.g., sodium or potassium), alkali metal hydrides (sodium hydride, lithium hydride), alkali metal aluminum hydrides (lithium aluminum hydride), alkali metal alkyls (n-butyllithium), Grignard reagents (methyl magnesium bromide, phenyl magnesium chloride), and the like. The deprotonation step is normally performed at or below room temperature, preferably at about room temperature, by combining the indenoindole compound and the deprotonating agent, usually in the presence of one or more dry organic solvents, especially ethers and/or hydrocarbons.

Suitable methods for generating dianionic indenoindolyl ligands (and their synthetic equivalents, such as trimethylsilyl-substituted indenoindoles) are also disclosed by T. Abraham et al. in *Monatsh. Chem.* 120 (1989) 117 and *Tetrahedron* 38 (1982) 1019. In a typical method, two equivalents of n-butyllithium are added slowly to an ice-cooled solution of the indenoindole in dry tetrahydrofuran to generate a blood-red solution of the dianion.

The first equivalent of base deprotonates the nitrogen atom and creates a sigma-electron donor center at nitrogen:

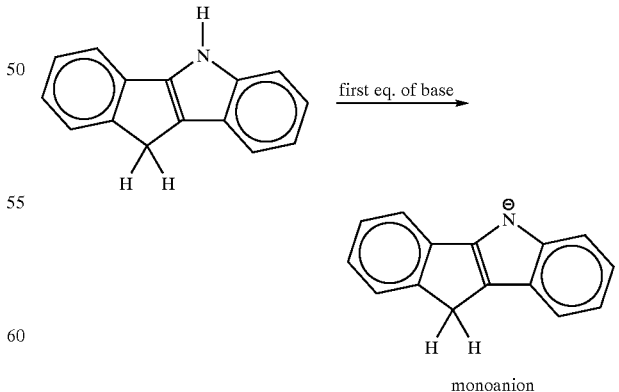

monoanion

Further deprotonation removes the cyclopentadienyl-like proton to generate a dianion that acts as a sigma- and pi-electron donor:

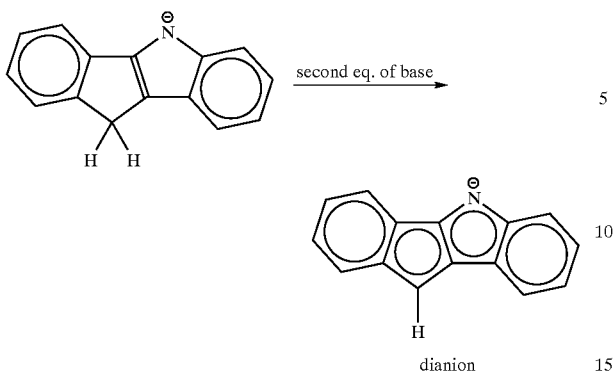

Reaction of the dianion with transition metal sources gives a complex that normally contains one or more indenoindolyl dianionic ligands that are π-and/or σ-bonded to the transition or lanthanide metal.

The indenoindolyl dianion preferably has a structure selected from:

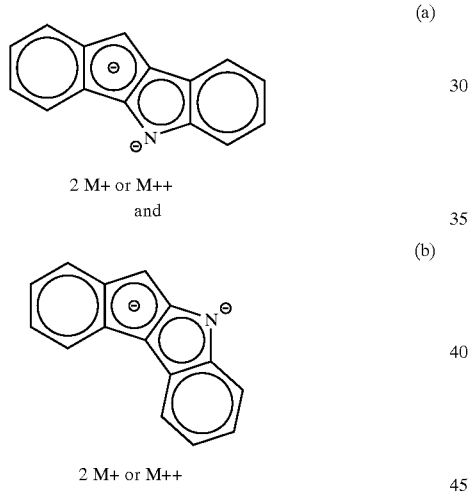

wherein M is a Group 1 (alkali) or Group 2 (alkaline earth) metal.

The invention contemplates the use of synthetic equivalents of indenoindolyl dianions in making the organometallic complexes. By "synthetic equivalent" of an indenoindolyl dianion, we mean a "masked" dianion. While not an indenoindolyl dianion per se, the synthetic equivalent has the ability to deliver one when reacted with a transition metal source (such as zirconium tetrachloride or cyclopentadienyltitanium trichloride). For a general discussion of synthetic equivalents, see F. A. Carey and R. J. Sundberg, *Advanced Organic Chemistry*, Part B (1977) pp. 418–419.

Suitable synthetic equivalents replace one or two acidic hydrogens from an indenoindole compound with an organosilicon, organotin, or organogermanium group. Examples (a)–(f) below illustrate various synthetic equivalents of indenoindolyl dianions.

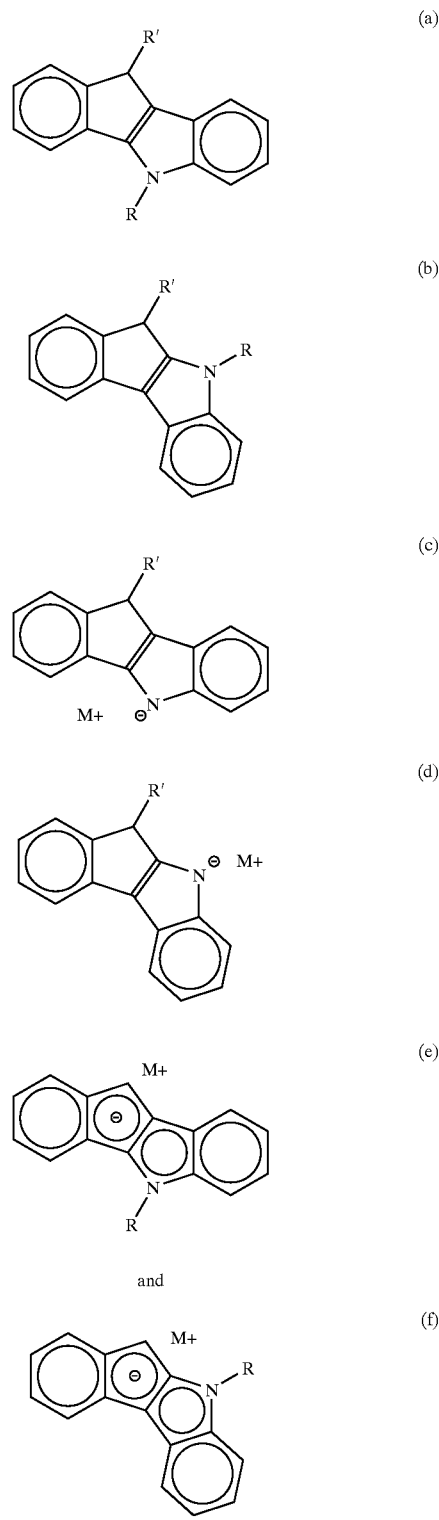

In the structures above, M is an alkali metal, and each of R and R' is independently selected from the group consisting of organotin, organosilicon, and organogermanium. Thus, suitable synthetic equivalents of the dianions can be neutral compounds that contain two organotin, -silicon, or -germanium groups; they can also be monoanionic compounds that have a single organotin, -silicon, or -germanium group.

When reacted with suitable transition metal sources, these synthetic equivalents readily give the desired indenoindolyl metal complex and an easily removed by-product, such as tri-n-butyltin chloride, dimethylamino(trimethyltin) or N,N-dimethyltrimethylsilylamine. The reaction of synthetic equivalent (X) below with one equivalent of tetrakis(dimethylamino)zirconium is illustrative:

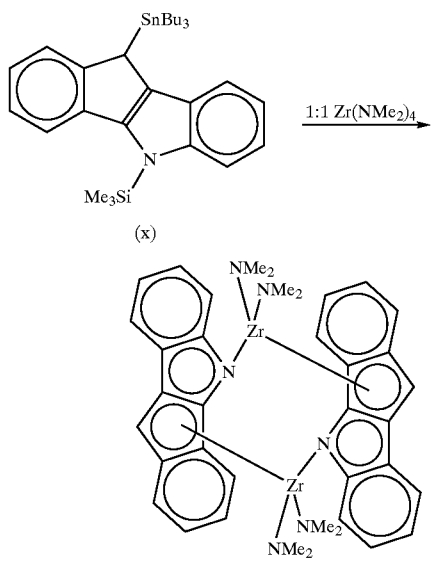

The synthetic equivalents can be made by numerous techniques. Some of these are described by Abraham et al. (see, especially, Scheme 3 in *Monatsh. Chem.* 120 at p. 122). Usually, a stepwise approach is used.

In one suitable method, an indenoindolyl N-centered monoanion is generated and reacted with chlorotrimethylsilane. (Optionally, the mixture is quenched with water and the N-silylated product is isolated.) Reaction with a second equivalent of base, typically n-butyllithium or the like, followed by reaction with another equivalent of chlorotrimethylsilane gives the desired disilylated product, which is a dianion synthetic equivalent:

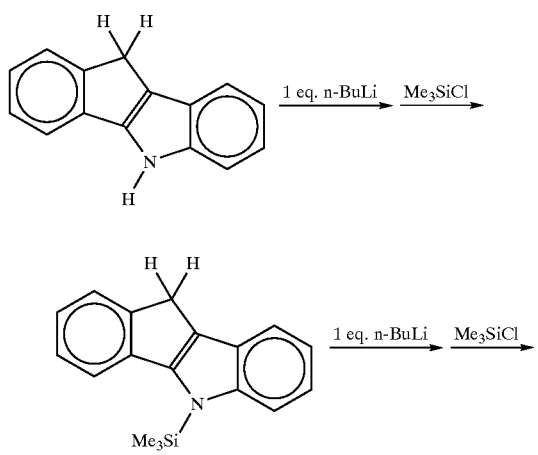

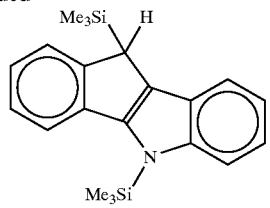

In another suitable method, a dianion is generated first, for example, with two equivalents of n-butyllithium. Reaction with one equivalent of chlorotrimethylsilane masks the more reactive cyclopentadienyl anion. (Again, the mixture is optionally quenched with water to isolate the C-silylated product.) Reaction with a second equivalent of chlorotrimethylsilane gives the same dianion synthetic equivalent:

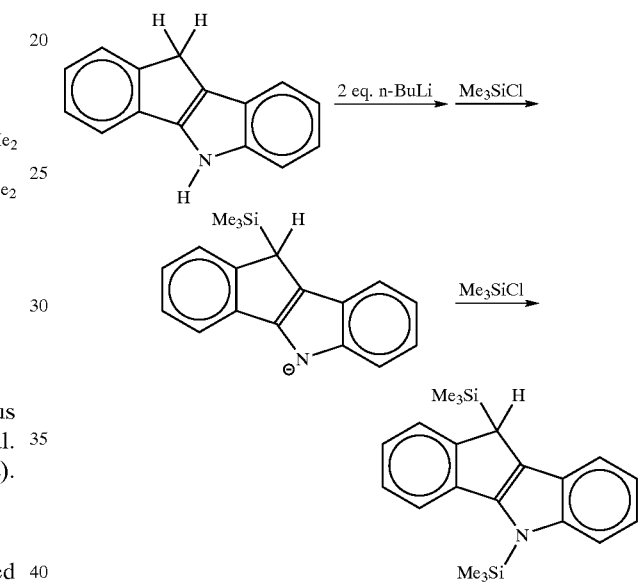

Similar strategies can be used to incorporate organotin, organosilicon, or organogermanium groups at either or both locations on the indenoindolyl ligand. Preparation of the synthetic equivalents takes advantage of well-established procedures for converting acidic N—H or C—H bonds, usually in two steps (deprotonation and nucleophilic displacement), to organosilicon-, organotin-, or organogermanium-substituted nitrogen or carbon.

Organometallic complexes of the invention are reaction products of a Group 3–10 transition or lanthanide metal compound and a dianionic indenoindolyl ligand or its synthetic equivalent. The Group 3–10 transition or lanthanide metal compound usually includes two or more labile anionic or neutral ligands that can be replaced by one or more indenoindolyl groups. Any convenient source of the Group 3 to 10 transition or lanthanide metal can be used. Usually, the source is a complex that contains one or more labile ligands that are easily displaced by the indenoindolyl dianion or synthetic equivalent. Examples are halides (e.g., $TiCl_4$, $ZrCl_4$), alkoxides, amides, and the like. The metal source can incorporate one or more of the polymerization-stable anionic ligands described below.

A diverse assortment of organometallic complexes can be made from indenoindolyl dianions and their equivalents. For example, monomeric, dimeric, or even polymeric organometallic complexes can be produced. The complexes can be mono-, bi-, or multimetallic. The complexes can exist in zwitterionic forms, and they can incorporate Group 13 atoms such as boron or aluminum.

One preferred complex has the structure:

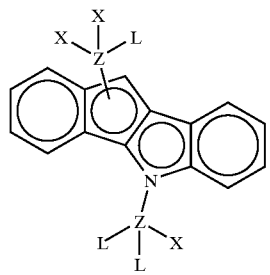

in which each Z is a Group 4 transition metal, each L independently represents a pi-donor ligand, and each X independently represents a sigma-donor ligand.

Preferred pi-donor ligands, L, include cyclopentadienyls, indenyls, fluorenyls, azaborolinyls, indolyls, and the like. These ligands are normally characterized as "polymerization stable" because they remain coordinated to the transition metal during olefin polymerizations. These and other suitable pi-donor ligands are described in U.S. Pat. Nos. 4,791,180 and 4,752,597, the teachings of which are incorporated herein by reference.

Suitable sigma-donor ligands, X, are normally labile groups such as halide, hydride, alkyl, aryl, aralkyl, alkoxy, aryloxy, dialkylamino, siloxy, or the like. Halides are preferred.

The organometallic complex can be essentially a dimer that incorporates two transition metal atoms and two indenoindolyl ligands. Such catalysts are conveniently made by reacting one equivalent of dianionic ligand or its equivalent with one equivalent of transition metal compound. Preferred complexes of this type have a structure selected from:

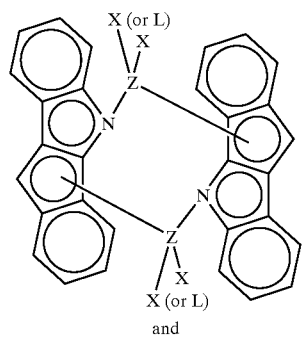
(a)

and

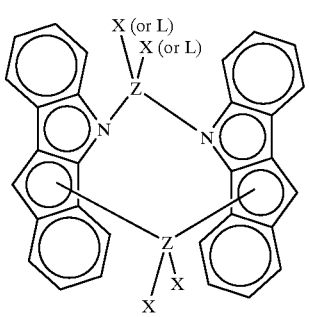
(b)

wherein Z, L, and X have the meanings defined earlier.

In making the dimer complexes as described above, polymeric complexes can comprise a minor or major portion of the reaction product. By modifying the reaction conditions, a skilled person can manipulate the proportion of dimer to polymeric complex to be produced. A preferred polymeric complex has the structure:

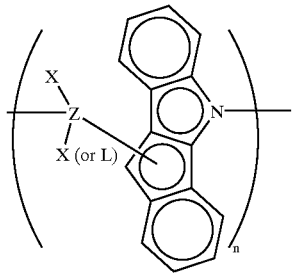

wherein Z, L, and X have the meanings defined earlier, and n has a value from about 2 to about 100.

Additional organometallic complexes of the invention comprise the reaction product of a Group 3–10 transition or lanthanide metal compound, a Group 13 compound, and a dianionic indenoindolyl ligand or its equivalent. One preferred complex of this type, which has one indenoindolyl group, has a structure selected from:

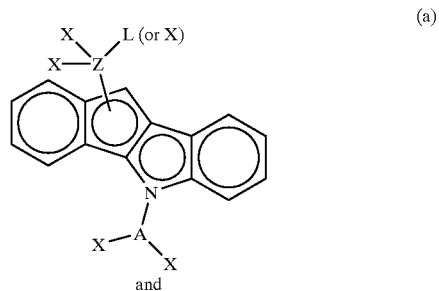
(a)

and

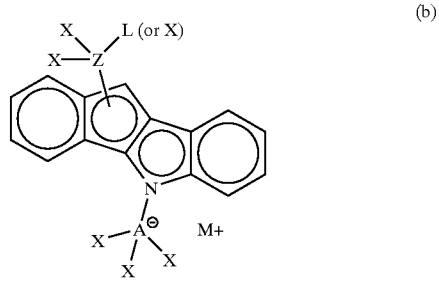
(b)

wherein M is an alkali metal, Z, L, and X have the meanings defined earlier, and A is a Group 13 element. Generally, these complexes are made by first reacting the nitrogen-centered monoanion with a Group 13 compound followed by deprotonation at the cyclopentadienyl fragment with a bulky base such as t-butyllithium, lithium diisopropylamide, 2,2,6,6-tetramethylpiperidinyl lithium, or the like. Subsequent reaction with a molar equivalent of the Group 3–10 (preferably Group 4) transition or lanthanide metal compound gives the desired bimetallic complex (a) above, and/or its quaternized equivalent (b).

Suitable Group 13 compounds are well known. These preferably have the formula $BX_3$ or $AlX_3$ wherein each X independently represents a labile sigma-donor ligand such as halide, hydride, alkyl, aryl, aralkyl, alkoxy, aryloxy, dialkylamino, siloxy, or the like. Halides and alkyls are preferred. Typical examples are chlorodimethylborane, chlorodiphenyl-borane, diethylaluminum chloride, triethylaluminum, ethylaluminum dichloride, and the like.

Complexes containing two indenoindolyl groups, a Group 13 element, and a Group 3–10 (preferably Group 4) element can also be made. Preferred complexes in this category have a structure selected from:

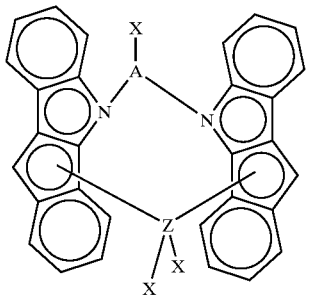

(a)

and

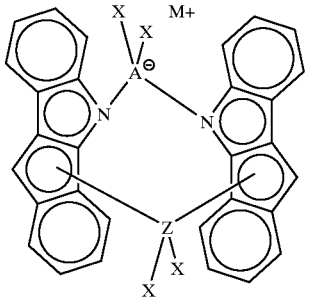

(b)

wherein M, Z, X, and A are as defined above.

Additional complexes incorporate a Group 3–10 transition or lanthanide metal, two Group 13 atoms, and two dianionic indenoindolyl ligands. Preferred complexes in this category have a structure selected from:

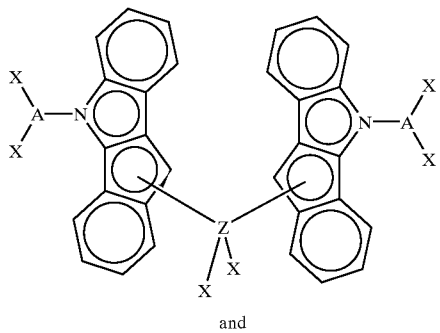

(a)

and

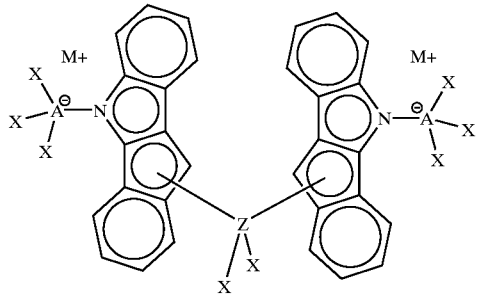

(b)

wherein M, Z, X, and A have the meanings defined earlier.

By adjusting the reaction conditions and proportions of reactants, polymeric complexes can also be made. Preferred polymeric complexes of this type have a structure selected from:

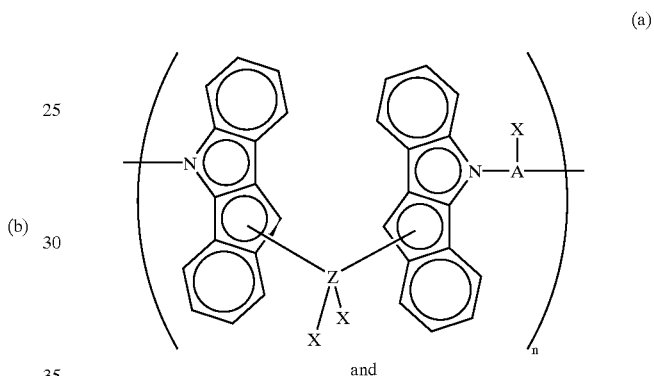

(a)

and

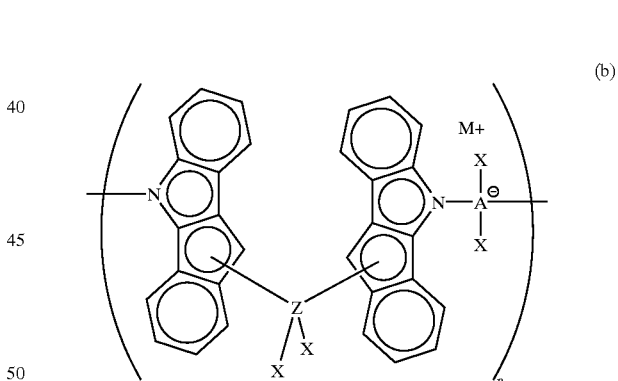

(b)

wherein M, Z, X, and A have the meanings defined above, and n has a value from about 2 to about 100.

Catalyst systems of the invention comprise the organometallic complex and an activator. Suitable activators ionize the organometallic complex to produce an active olefin polymerization catalyst. Suitable activators are well known in the art. Examples include alkyl alumoxanes (methyl alumoxane (MAO), PMAO, ethyl alumoxane, diisobutyl alumoxane), alkylaluminum compounds (triethylaluminum, diethyl aluminum chloride, trimethylaluminum, triisobutyl aluminum), and the like. Suitable activators include acid salts that contain non-nucleophilic anions. These compounds generally consist of bulky ligands attached to boron or aluminum. Examples include lithium tetrakis (pentafluorophenyl)borate, lithium tetrakis (pentafluorophenyl)aluminate, anilinium tetrakis(pentafluorophenyl)borate, and the like. Suitable activators also include organoboranes, which include boron and one or more alkyl, aryl, or aralkyl groups. Suitable activators include substituted and unsubstituted trialkyl and triarylboranes such as tris(pentafluorophenyl)borane, triphenylborane, tri-n-octylborane, and the like. These and other suitable boron-containing activators are described in U.S. Pat. Nos. 5,153,157, 5,198,401, and 5,241,025, the teachings of which are incorporated herein by reference. Alkyl alumoxanes such as MAO are most preferred.

The amount of activator needed relative to the amount of organometallic complex depends on many factors, including the nature of the complex and activator, the desired reaction rate, the kind of polyolefin product, the reaction conditions, and other factors. Generally, however, when the activator is an alkyl alumoxane or an alkyl aluminum compound, the amount used will be within the range of about 0.01 to about 5000 moles, preferably from about 0.1 to about 500 moles, of aluminum per mole of transition metal. When the activator is an organoborane or an ionic borate or aluminate, the amount used will be within the range of about 0.01 to about 5000 moles, preferably from about 0.1 to about 500 moles, of activator per mole of transition metal.

If desired, a catalyst support such as silica or alumina can be used. However, the use of a support is generally not necessary for practicing the process of the invention.

The catalysts are particularly valuable for polymerizing olefins. Preferred olefins are ethylene and $C_3$–$C_{20}$ α-olefins such as propylene, 1-butene, 1-hexene, 1-octene, and the like. Mixtures of olefins can be used. Ethylene and mixtures of ethylene with $C_3$–$C_{10}$ α-olefins are especially preferred.

Many types of olefin polymerization processes can be used. Preferably, the process is practiced in the liquid phase, which can include slurry, solution, suspension, or bulk processes, or a combination of these. High-pressure fluid phase or gas phase techniques can also be used. The process of the invention is particularly valuable for solution and slurry processes.

The olefin polymerizations can be performed over a wide temperature range, such as about –30° C. to about 280° C. A more preferred range is from about 30° C. to about 180° C.; most preferred is the range from about 60° C. to about 100° C. Olefin partial pressures normally range from about 15 psia to about 50,000 psia. More preferred is the range from about 15 psia to about 1000 psia.

Catalyst concentrations used for the olefin polymerization depend on many factors. Preferably, however, the concentration ranges from about 0.01 micromoles per liter to about 100 micromoles per liter. Polymerization times depend on the type of process, the catalyst concentration, and other factors. Generally, polymerizations are complete within several seconds to several hours.

The examples below illustrate the preparation of an indenoindolyl dianion, its incorporation into a bimetallic Group 4 metal complex, and the use of a catalyst system that includes the complex for polymerizing ethylene. As the examples show, the catalysts are easy to make and have good activity.

The following examples merely illustrate the invention. Those skilled in the art will recognize many variations that are within the spirit of the invention and scope of the claims.

Ligand Precursor Preparation

8-Methyl-5,10-dihydroindeno[1,2-b]indole (I), the ligand precursor of the catalyst prepared in Example A, is prepared by the method of Buu-Hoi and Xuong (J. Chem. Soc. (1952) 2225) by reacting p-tolylhydrazine with 1-indanone in the presence of sodium acetate/ethanol:

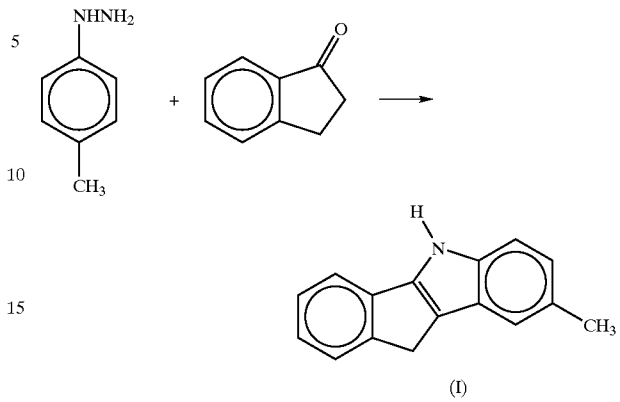

EXAMPLE A

Preparation of Bimetallic Catalyst from Indenoindolyl Dianion

8-Methyl-5,10-dihydroindeno[1,2-b]indole (I) (0.219 g, 1.00 mmol) is dissolved in tetrahydrofuran (THF) (25 mL) and is stirred under nitrogen. n-Butyllithium (1.0 mL of 2.0 M solution in hexanes, 2.0 mmol) is added, and the mixture is stirred at room temperature for 30 min. The resulting dianion solution (1.0 mmol) is added to a solution of zirconium tetrachloride bis(tetrahydrofuran) complex (0.377 g, 1.0 mmol) in THF (20 mL). Evaporation of solvent gives an orange solid (0.582 g), presumably a mixture of LiCl and the desired bimetallic complex (II) and polymeric by-products.

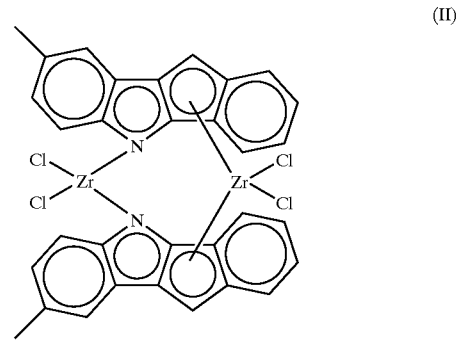

EXAMPLE B

Ethylene Polymerization

A 1.7-L, stainless-steel stirred reactor is purged with nitrogen, sealed, and charged with hydrogen (Δ60 psi from a cylinder having V=7.0 $cm^3$). Triisobutylaluminum (1.18 mL of a 1.00 M solution in isobutane) is injected into the reactor, followed by 1-butene (200 mL) and isobutane (600 mL). The reactor is heated to 70° C. and allowed to equilibrate. Ethylene is introduced to give a total pressure in the reactor of 350 psig, and the reactor is again equilibrated. A solution of PMAO (1.2 mL of 2.22 M solution in toluene), a portion of the bimetallic complex (II) from Example A (4.0 mg, 0.0044 mmol), and isobutane (200 mL) is injected into the reactor to start the polymerization. Ethylene is fed on demand to keep the reactor pressure at 350 psig. After 30 min., the ethylene flow is stopped, and the reaction mixture is cooled to room temperature. The yield of polyethylene (mp 127° C.) is 11.4 g. Catalyst activity: 5700 grams of polymer per gram Zr per hour.

The preceding examples are meant only as illustrations. The following claims define the invention.

I claim:

1. An organometallic complex which comprises:
   (a) at least one Group 3–10 transition or lanthanide metal; and
   (b) at least one dianionic indenoindolyl ligand that is pi- or sigma-bonded to the metal.

2. A bimetallic complex of claim 1.

3. The complex of claim 1 wherein the dianionic indenoindolyl ligand has a structure selected from the group consisting of:

(a)

2 M+ or M++ and (b)

2 M+ or M++ wherein M is a Group 1 or Group 2 metal.

4. The complex of claim 1 wherein the dianionic indenoindolyl ligand is generated from a synthetic equivalent.

5. The complex of claim 4 wherein the synthetic equivalent has one or two organotin, organosilicon, or organogermanium groups attached to nitrogen and/or the cyclopentadienyl ring of the ligand.

6. The complex of claim 5 wherein the synthetic equivalent has a structure selected from the group consisting of:

(a)

(b)

-continued (c)

(d)

(e)

and (f)

wherein M is an alkali metal, and each of R and R' is independently selected from the group consisting of organotin, organosilicon, and organogermanium.

7. The complex of claim 1 having the structure:

in which each Z is a Group 4 transition metal, and wherein each L independently represents a pi-donor ligand and each X independently represents a sigma-donor ligand.

8. The complex of claim 1 having a structure selected from the group consisting of:

(a)

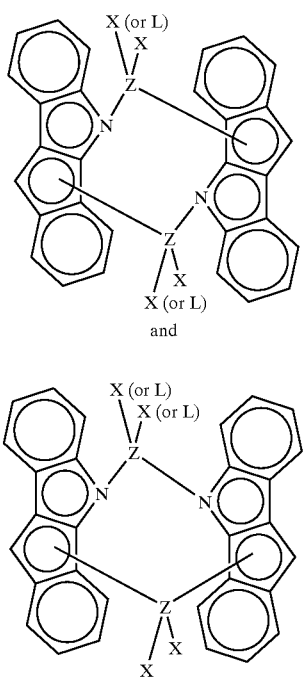

and (b)

wherein each Z is a Group 4 transition metal, each L independently represents a pi-donor ligand, and each X independently represents a sigma-donor ligand.

9. A polymeric complex of claim 1 having the structure:

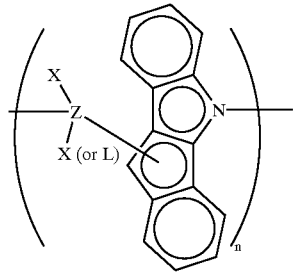

wherein Z is a Group 4 transition metal, L is a pi-donor ligand, each X independently represents a sigma-donor ligand, and n has a value from about 2 to about 100.

10. An organometallic complex which comprises:

(a) at least one Group 3–10 transition or lanthanide metal;

(b) at least one Group 13 element; and (c) at least one dianionic indenoindolyl ligand that is pi- or sigma-bonded to the Group 3–10 metal and is sigma-bonded to the Group 13 element.

11. The complex of claim 10 having a structure selected from the group consisting of:

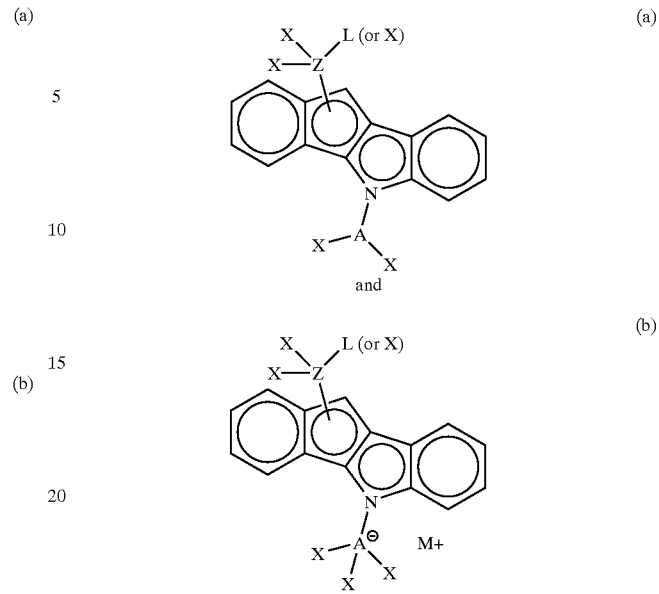

wherein M is an alkali metal, Z is a Group 4 transition metal, A is a Group 13 element, L is a pi-donor ligand, and each X independently represents a sigma-donor ligand.

12. The complex of claim 10 having a structure selected from the group consisting of:

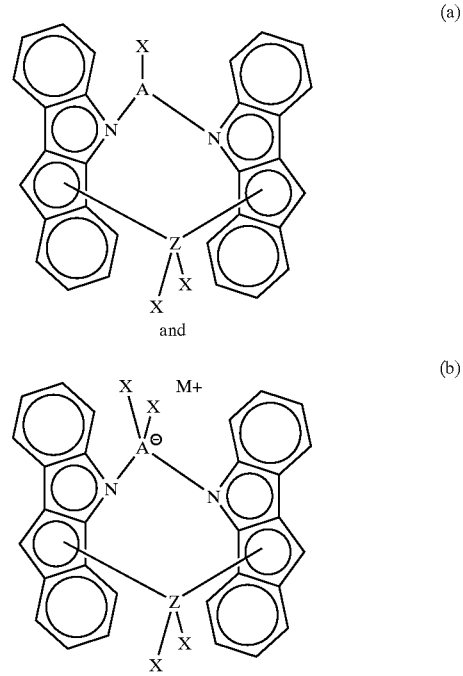

wherein M is an alkali metal, Z is a Group 4 transition metal, A is a Group 13 element, and each X independently represents a sigma-donor ligand.

13. The complex of claim 10 having a structure selected from the group consisting of:

(a)

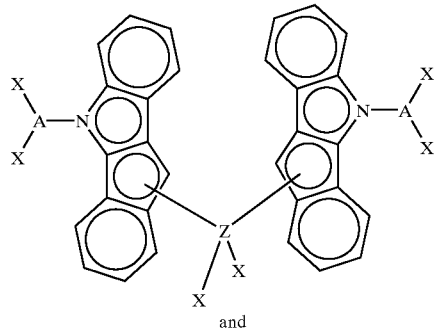

and (b)

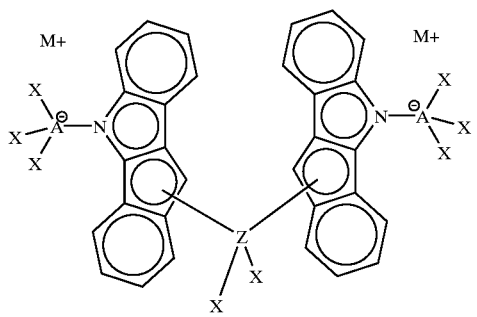

wherein M is an alkali metal, Z is a Group 4 transition metal, A is a Group 13 element, and each X independently represents a sigma-donor ligand.

14. A polymeric complex of claim 10 having a structure selected from the group consisting of:

(a)

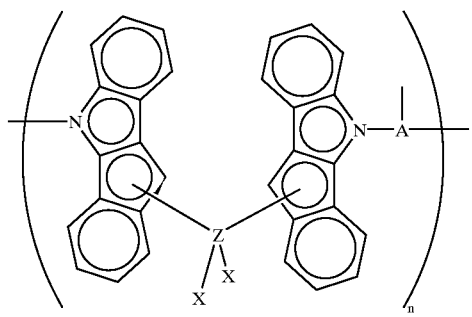

-continued
and (b)

wherein M is an alkali metal, Z is a Group 4 transition metal, A is a Group 13 element, each X independently represents a sigma-donor ligand, and n has a value from about 2 to about 100.

15. A catalyst system which comprises an activator and the complex of claim 1.

16. The catalyst system of claim 15 wherein the activator is an alkyl alumoxane.

17. A catalyst system which comprises an activator and the complex of claim 10.

18. The catalyst system of claim 17 wherein the activator is an alkyl alumoxane.

19. A method which comprises polymerizing an olefin in the presence of the catalyst system of claim 15.

20. A method which comprises polymerizing an olefin in the presence of the catalyst system of claim 17.

* * * * *